(12) United States Patent
Hildebrand et al.

(10) Patent No.: US 12,429,469 B2
(45) Date of Patent: Sep. 30, 2025

(54) METHOD AND DEVICE FOR OPERATING A GAS SENSOR

(71) Applicant: Robert Bosch GmbH, Stuttgart (DE)

(72) Inventors: Felix Eberhard Hildebrand, Stuttgart-West (DE); Matthias Martin Hanauer, Leonberg (DE); Stefan Falkner, Renningen (DE); Ulrich Sauter, Karlsruhe (DE)

(73) Assignee: ROBERT BOSCH GMBH, Stuttgart (DE)

( * ) Notice: Subject to any disclaimer, the term of this patent is extended or adjusted under 35 U.S.C. 154(b) by 320 days.

(21) Appl. No.: 17/785,144

(22) PCT Filed: Dec. 21, 2020

(86) PCT No.: PCT/EP2020/087501
§ 371 (c)(1),
(2) Date: Jul. 13, 2022

(87) PCT Pub. No.: WO2021/123443
PCT Pub. Date: Jun. 24, 2021

(65) Prior Publication Data
US 2023/0010457 A1    Jan. 12, 2023

(30) Foreign Application Priority Data
Dec. 20, 2019   (DE) .................... 10 2019 220 455.4

(51) Int. Cl.
*G01N 33/00*    (2006.01)
*G06F 17/18*    (2006.01)
(Continued)

(52) U.S. Cl.
CPC ......... *G01N 33/0006* (2013.01); *G06F 18/21* (2023.01); *G06F 30/27* (2020.01); *G06F 17/18* (2013.01)

(58) Field of Classification Search
CPC ..... G01N 33/0006; G06F 18/21; G06F 30/27; G06F 17/18
See application file for complete search history.

(56) References Cited

U.S. PATENT DOCUMENTS 5,554,273 A    9/1996  Demmin et al.
9,213,016 B1   12/2015  Stetter et al.
(Continued)

FOREIGN PATENT DOCUMENTS

CN    1514239 A    *   7/2004
CN    103544392 A  *   1/2014
(Continued)

OTHER PUBLICATIONS

Machine translation for CN-103544392-A, downloaded 2024 (Year: 2024).*

(Continued)

*Primary Examiner* — John C Kuan
(74) *Attorney, Agent, or Firm* — NORTON ROSE FULBRIGHT US LLP

(57) ABSTRACT

A method for operating a gas sensor system comprising a gas sensor, in order to provide a concentration variable of a gas concentration of a gas component in a sample gas. The method includes: measuring the gas concentration during a measurement process in order to obtain a temporal evolution of a sensor signal as a function of the gas concentration; determining the concentration variable using a data-based sensor model as a function of the temporal evolution of the sensor signal, the data-based sensor model being trained to take into account a behavior of the sensor outside the measurement process in order to ascertain the concentration variable.

31 Claims, 2 Drawing Sheets

(51) Int. Cl.
*G06F 18/21* (2023.01)
*G06F 30/27* (2020.01)

(56) References Cited

U.S. PATENT DOCUMENTS

| | | | |
|---|---|---|---|
| 2006/0155486 A1* | 7/2006 | Walsh | G01N 33/0034 702/32 |
| 2019/0170679 A1 | 6/2019 | Ross | |
| 2020/0355662 A1* | 11/2020 | Carbonelli | G01N 33/0034 |
| 2020/0400637 A1* | 12/2020 | Rahim | G01N 33/0075 |

FOREIGN PATENT DOCUMENTS

| | | | |
|---|---|---|---|
| CN | 104713985 A * | 6/2015 | |
| CN | 106405007 B | 10/2018 | |
| CN | 109472303 A | 3/2019 | |
| DE | 29810753 U1 | 11/1998 | |
| DE | 19818329 A1 | 10/1999 | |
| DE | 10202869 A1 | 8/2003 | |
| JP | H0629566 A | 2/1994 | |
| JP | H0636180 Y2 | 9/1994 | |
| JP | H07103923 A | 4/1995 | |
| JP | H09257668 A | 10/1997 | |
| JP | H10227655 A | 8/1998 | |
| JP | 2001074680 A | 3/2001 | |
| JP | 2009216610 A | 9/2009 | |
| JP | 2011002400 A | 1/2011 | |
| JP | 2018112510 A | 7/2018 | |
| JP | 2019090805 A | 6/2019 | |
| JP | 2019095264 A | 6/2019 | |
| JP | 2019164049 A | 9/2019 | |
| WO | 2006062726 A1 | 6/2006 | |
| WO | 2019128203 A1 | 7/2019 | |

OTHER PUBLICATIONS

Zhao et al., "Sensor Drift Compensation Based on the Improved LSTM and SVM Multi-Class Ensemble Learning Models" Sensors 2019, 19, 3844 (Year: 2019).*
International Search Report for PCT/EP2020/087501 Issued Mar. 31, 2021.

* cited by examiner

METHOD AND DEVICE FOR OPERATING A GAS SENSOR

FIELD

The present invention relates to gas sensors, and in particular to methods for determining a concentration value, taking into account storage-induced changes to the sensitivity of gas sensors.

BACKGROUND INFORMATION

Conventional gas sensors for determining concentrations of gaseous substances may in principle be designed as chemical sensors with various sensor principles and sensitive materials. Generally, a chemical reaction or absorption of a gaseous component to be measured at a sensitive layer in the sensor assembly leads to a change in the properties of the sensitive layer. This change in the properties of the sensitive layer may be detected as a change in an electrical variable and evaluated.

Depending on the sensor material used, the behavior of the gas sensor is more or less stable, and the state of the gas sensor may thus change over its lifetime, depending on environmental conditions. Particularly during periods of storage, the sensor properties may change over the course of a storage period due to influences such as ambient temperature, atmospheric humidity, contamination of the surrounding air and the like, such that a reliable and accurate determination of a gas concentration of a gas component in a sample gas is no longer possible. This problem occurs above all in gas sensors in which organic materials and in particular organic semiconductors are used in the sensitive layer, since signal-changing molecules may be absorbed or released in the sensitive layer during storage periods.

SUMMARY

According to the present invention, a method for operating a gas sensor, a device, and a gas sensor are provided.

Example embodiments of the present invention are disclosed herein.

According to a first aspect of the present invention, a method is provided for operating a gas sensor system comprising a gas sensor, in order to provide a concentration variable of a gas concentration of a gas component in a sample gas. In accordance with an example embodiment of the present invention, the method comprises the following steps:

measuring the gas concentration during a measurement process in order to obtain a temporal evolution of a sensor signal as a function of the gas concentration;

determining the concentration variable as a function of the temporal evolution of the sensor signal with the aid of a data-based sensor model which takes into account a behavior of the sensor outside the measurement process in order to ascertain the corrected concentration variable.

The above example method provides for ascertaining a gas concentration of a gas component to be detected in the sample gas in the form of a concentration variable, based on an observation of a time-dependent sensor signal over the course of a measurement process during which a sensitive layer is exposed to sample gas, and based on a behavior of the sensor outside the period of the measurement process. Evaluating the sensor behavior outside the period of the measurement process makes it possible to take account of the storage-induced and/or aging-induced sensor state when ascertaining the gas concentration.

In the above method, it is assumed in particular that the sensor behavior outside the time of the actual measurement process is characteristic of the sensor state in general. Since the actual sensor state is not usually directly measurable and/or quantifiable, the sensor state may be taken into account implicitly with the aid of the trainable data-based sensor model when ascertaining the gas concentration of the gas components to be detected, depending on the sensor behavior. Thus, for example, the behavior of the sensor signal during heating-up and cooling-down phases preceding and/or following the period of the measurement process may allow conclusions to be drawn about the storage-induced and/or aging-induced sensor state.

Therefore, in accordance with an example embodiment of the present invention, a sensor model may be created or provided which, based on the sensor signals during the measurement and based on sensor signals and/or operating parameters of the gas sensor that are independent of the measurement process, contributes to a determination of a more accurate concentration value of the gas component to be detected in the sample gas.

In particular, device-specific calibration parameters and sensor states, such as a sensor temperature, a sample gas temperature and a measurement humidity, may be taken into consideration as operating parameters. A device-specific calibration parameter may generally indicate device-specific and/or sensor-specific information, in particular the sensitivity of the gas sensor.

Moreover, these operating parameters may also be considered as time series. Thus, for example, the evolution of the gas temperature of the sample gas, the evolution of the gas humidity of the sample gas, and the evolution and humidity of a purging gas with which the gas sensor is purged outside the measurement processes, may be taken into account.

Any type of regression algorithms, such as Lasso, random forest, Gaussian process and neural networks, for example, may be used as the data-based sensor model. In particular, data-based models are preferred which are translation invariant relative to the duration of the individual time periods, such as the time period for the measurement process or for a preceding or subsequent heating-up, cooling-down and holding phase, depending on the sensor operating mode in the measurement procedure, as is the case with convolutional neural networks, for example.

In particular, the data-based sensor model may be trained to take account of a sensor behavior influenced by an aging or degradation of the gas sensor in order to ascertain the concentration variable.

Using the above method, it is possible to take better account of the storage-induced and aging-induced changes in sensor states when determining a gas concentration. This is achieved by evaluating the behavior of the gas sensor, which is dependent on the storage-induced and aging-induced sensor state, particularly outside the period of the measurement process, such that a precise evaluation of the sensor signal received during the measurement process is always possible.

The above method represents a significant improvement over conventional calibration methods, since those are merely static and are unable to take sufficient account of sensor states that change over time. In addition, conventional calibration methods are laborious and cannot usually be carried out at the place of use.

In accordance with an example embodiment of the present invention, it may be provided that the data-based sensor model is used to ascertain a correction variable to be applied to a physically modeled concentration variable, in particular by multiplication or addition, the physically modeled concentration variable being determined on the basis of measurement variables associated with the measurement process.

Alternatively, the data-based sensor model may be designed to determine the concentration variable as a function of the temporal evolution of the sensor signal and as a function of the sensor behavior outside the measurement process.

In particular, the corrected concentration variable may be ascertained as a function of a physically modeled concentration variable and as a function of a concentration variable ascertained from the sensor model, in particular in accordance with a predefined weighting function.

In accordance with an example embodiment of the present invention, it may be provided that the data-based sensor model receives as input variables measurement variables associated with the measurement process and measurement features derived therefrom.

In particular, the measurement variables may comprise one or more variables that result from the time-dependent sensor signal over the period of the measurement process, in particular values of the sensor signal at a plurality of sampling times between the start and end of the measurement process and/or one or more variables derived therefrom, in particular an absolute signal change in the sensor signal between start and end of the measurement process and/or the maximum or average increase in the sensor signal S during the measurement process.

Furthermore, in accordance with an example embodiment of the present invention, the measurement variables may comprise one or more variables that result from the temporal sensor signal over a period outside the period of the measurement process, in particular over a period preceding and/or following the exposure phase, in particular over a period during which a specific sensor state is established, in particular values of the sensor signal at a plurality of sampling times between the start and end of the period in question and/or of one or more variables derived therefrom, in particular an absolute signal change between start and end of the period in question and/or the maximum or average increase in the sensor signal S over the period in question.

In accordance with an example embodiment of the present invention, it may be provided that the measurement variables comprise one or more of the following variables:
one or more device-specific and/or sensor-specific calibration parameters, which indicate in particular a sensitivity of the gas sensor;
one or more variables that result from a temporal signal of one or more further sensors integrated in the system, in particular a sample gas temperature sensor, a sample gas humidity sensor and a gas sensor temperature sensor, over the period of the measurement process and/or a period outside the period of the measurement process, in particular values of the corresponding signal at a plurality of sampling times between the start and end of the measurement process or of the period in question and/or of one or more variables derived therefrom, in particular an absolute signal change between start and end of the period in question and/or the maximum or average increase in the signal of the one or more further sensors integrated in the system over the period in question; and
one or more variables that result from the difference between the time-dependent signal of one or more sensors integrated in the system, in particular the gas sensor, over the period of the measurement process and/or a period outside the period of the measurement process, and the time-dependent signal of the same sensor/sensors in the same period of a previous measurement, in particular a calibration measurement, in particular values of the corresponding difference at a plurality of sampling times between the start and end of the measurement process or of the period in question and/or of one or more variables derived therefrom.

Furthermore, the measurement features may be derived from the measurement variables and may comprise one or more of the following variables:
an indication of a signal response triggered by application of a test voltage pulse;
a proportionality factor between the temperature and the sensor signal and/or a time constant of the signal response;
one or more signal responses triggered by sudden changes in the composition and/or pressure of the sample gas meeting the sensor surface (31);
a baseline value corresponding to a raw gas sensor signal at a defined point in time, in particular at the time of the start of the measurement process;
one or more parameters of physical models that are fitted to the measurement data;
a parameter of an exponential function that is fitted to the sensor signal during the heating-up or cooling-down phase;
one or more modified measurement variables, in particular by compensation of the influence of temperature on the sensor signal using a corresponding proportionality factor;
one or more discrete values of the sensor signal in time periods before or after the measurement process as a function of the temperature; and
a difference or quotient between successively detected values of at least one of the measurement variables, in particular a difference or quotient between successively detected values of at least one of the measurement variables between a current value of the at least one measurement variable and a reference value of the at least one measurement variable.

According to a further aspect of the present invention, a device is provided for operating a gas sensor system comprising a gas sensor in order to provide a concentration variable of a gas concentration of a gas component in a sample gas. In accordance with an example embodiment of the present invention, the device is configured to:
measure the gas concentration during a measurement process in order to obtain a temporal evolution of a sensor signal as a function of the gas concentration; and
determine the concentration variable as a function of the temporal evolution of the sensor signal using a data-based sensor model which is trained to take into account a behavior of the sensor outside the measurement process in order to ascertain the concentration variable.

According to a further aspect of the present invention, a gas sensor system comprising a gas sensor and the above device is provided.

BRIEF DESCRIPTION OF THE DRAWINGS

Specific embodiments are described in detail below by reference to the figures.

DETAILED DESCRIPTION OF EXAMPLE EMBODIMENTS

Figure 1:
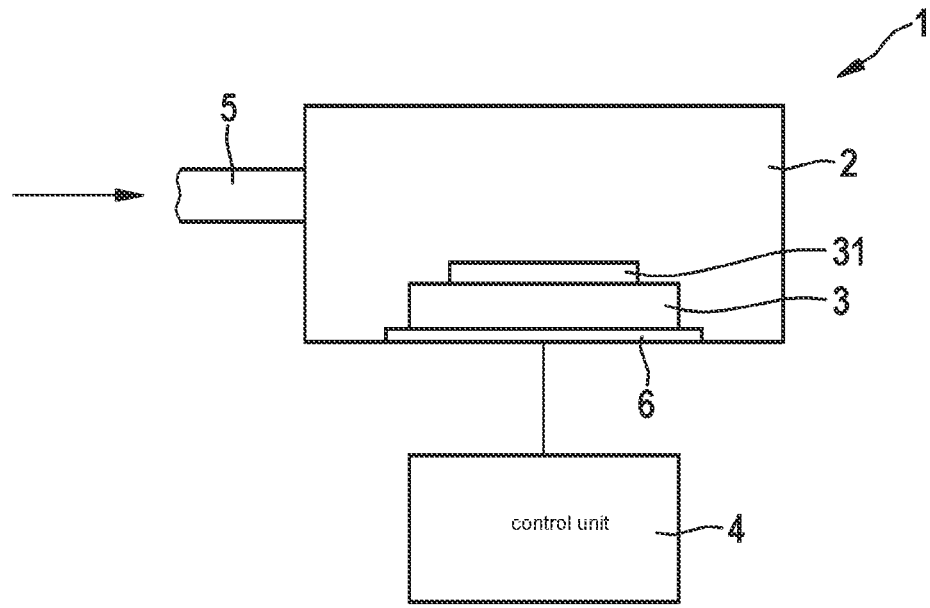
FIG. 1 shows a schematic representation of a gas sensor, in accordance with an example embodiment of the present invention.

FIG. 1 shows a schematic representation of a gas sensor system 1 comprising a measuring chamber 2, in which a gas sensor 3 is arranged. Gas sensor 3 has a sensor surface 31 with a sensitive layer, which is exposed to the gas component to be detected and which provides an electrical sensor variable that indicates a gas concentration of the gas component to be detected.

Controlled by a control unit 4, a sample gas in which a concentration of a gas component to be detected is to be measured may be introduced into measuring chamber 2 via a gas inlet 5. Moreover, a purging gas may be introduced into measuring chamber 2 in order to calibrate gas sensor 3. The sample gas is usually discharged via a further channel, such that the sample gas flows continuously over gas sensor 3.

Control unit 4 may be provided locally or be implemented in a cloud-based manner and may be in communication connection with gas sensor 3.

Gas sensor 3 is provided with a heater 6 for heating gas sensor 3 to various temperature levels.

Gas sensors may have various measuring principles. In particular, semiconductor gas sensors may be operated in a temperature cycle mode, in which oxygen accumulates at the sensor surface in a high-temperature phase. The oxygen is then displaced by the gas component to be detected during a low-temperature phase. The change in conductivity in the low-temperature phase may then be evaluated in an appropriate manner in order to obtain a gas concentration. Alternatively, the gas concentration of the gas component to be detected in the sample gas may also be ascertained from the conductivity of the semiconductor gas sensor when the sensor surface of gas sensor 3 is in an equilibrium state.

Other gas sensor measuring principles also provide for temporal phases with different thermal loading regimes.

Gas sensor 3 is generally designed in such a way that a chemical reaction, adsorption or absorption of a gas component to be detected and measured at sensor surface 31 leads to a change in the properties of sensor surface 31, reflected in a change in an electrical sensor variable (sensor signal), for example in the form of a change in sensor current, sensor voltage or sensor resistance (sensor conductivity).

Owing to external influences, such as temperature, atmospheric humidity and material exposure, gas sensor 3 is subject over its lifetime to a change of state, which changes the sensor state and hence the sensor sensitivity. This results in a storage-induced and aging-induced miscalibration of the gas sensors, which should be compensated. Conventional methods propose recalibrations, which are laborious and are only carried out at specific times, between which gas sensor 3 is not properly calibrated.

In principle, a concentration variable is to be provided with the aid of gas sensor system 1. The concentration variable indicates the gas concentration of a gas component to be detected in a sample gas washing over sensor surface 31. Aging influences and environmental influences on a gas sensor 3 are to be taken into account here. To ascertain these influences on the concentration measurement due to a change in a storage-induced and aging-induced sensor state, a data-based sensor model is used in control unit 4 and is trained either

- to determine a correction variable to apply to the concentration variable derived from the measured sensor variable, or
- to determine the concentration variable directly from the evolution of the electrical sensor variable during a concentration measurement and from further operating parameters and/or behavior parameters of gas sensor 3.

Figure 2:
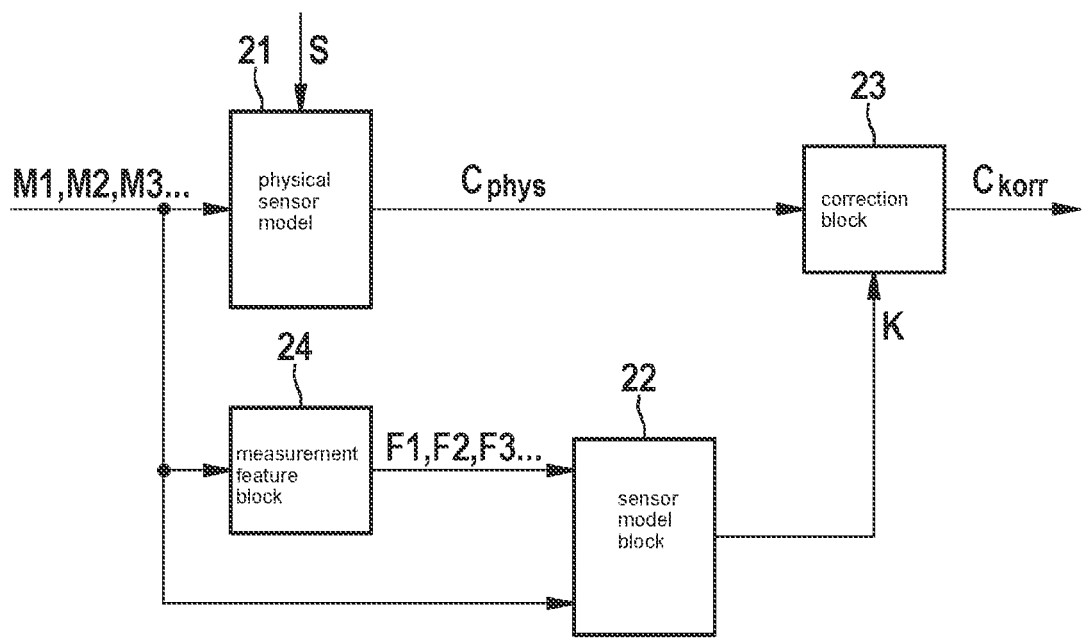
FIG. 2 shows a block diagram to illustrate a function for determining a gas concentration using a gas sensor according to a first specific embodiment of the present invention.

A functional diagram illustrating a process of ascertaining the concentration variable for the gas concentration of a gas component based on a correction variable ascertained by the data-based sensor model is shown in FIG. 2. To this end, a physical sensor model 21, created on the basis of physical rules and depending on the specific sensor technology, is used to determine a raw concentration variable $C_{phys}$, which indicates a gas concentration for an unchanged (e.g., not aged, or in the as-manufactured state) gas sensor 3. In principle, the underlying physical sensor model 21 may indicate the sensor sensitivity of a new, non-aged gas sensor 3.

Physical sensor model 21 may be, for example, any mathematical function, such as a series expansion, for example, which typically includes a relatively large number of model parameters, or the like. The model parameters of the physical sensor model are usually globally optimized and are calibrated specifically for the device, and are thus fixed for the individual gas sensor 3.

The raw concentration variable $C_{phys}$ may be determined in sensor model 21 as a function of the sensor signal S and of one or more of the following measurement variables M1, M2, M3, . . . :

- variables that result from the time-dependent sensor signal S over the period of the measurement process, i.e., during the phase of exposure to the sample gas, such as, e.g., values of the sensor signal at a plurality of sampling times between the start and end of the measurement process and/or variables derived therefrom, such as, e.g., the absolute signal change between start and end of the measurement process or the maximum or average increase in the sensor signal S during the measurement process.
- variables that result from the temporal sensor signal over a period outside the period of the measurement process, in particular over a period preceding and/or following the exposure phase, and in particular over a period during which a specific sensor state is established, in particular over a period of a predefined temperature evolution, in particular a heating-up, cooling-down or temperature-holding phase, such as, e.g., values of the sensor signal at a plurality of sampling times between the start and end of the period in question and/or variables derived therefrom, such as, e.g., the absolute signal change between start and end of the period in question or the maximum or average increase in the sensor signal S over the period in question;
- one or more device-specific calibration parameters which contribute to the accuracy of the model by providing device-specific information, in particular the sensitivity of the gas sensor, depending on its type. These calibration parameters may be predefined and/or determined empirically.

variables that result from a temporal signal of one or more further sensors integrated in the system, such as for example a sample gas temperature sensor, a sample gas humidity sensor and a gas sensor temperature sensor, over the period of the measurement process and/or a period outside the period of the measurement process, such as, e.g., values of the sensor signal at a plurality of sampling times between the start and end of the measurement process or of the period in question and/or of one or more variables derived therefrom, in particular an absolute signal change between start and end of the period in question and/or the maximum or average increase in the signal of the one or more further sensors integrated in the system over the period in question.

one or more variables that result from the difference between the time-dependent signal of one or more sensors integrated in the system, in particular the sensor signal S, over the period of the measurement process and/or a period outside the period of the measurement process, and the time-dependent signal of the same sensor/sensors in the same period of a previous measurement, in particular a calibration measurement, in particular values of the corresponding difference at a plurality of sampling times between the start and end of the measurement process or of the period in question and/or of one or more variables derived therefrom.

For example, the raw concentration variable $c_{phys}$ may be calculated on the basis of one of the following models parameterized with model parameters a, b, c . . . from the measurement variables M1, M2, ascertained in this way, using:

a linear model according to $$C_{phys}=aM1+bM2+cM3+d$$

a power model according to $$C_{phys}=aM1^b+cM2^d+eM3^f+\ldots+h$$

or a physical model, assuming Langmuir adsorption and disregarding desorption processes during the measurement process, according to $$C_{phys}=f(M1,M2,M3\ldots a,b,c)$$

In a sensor model block 22, a correction variable K is now ascertained, to which the raw concentration variable $C_{phys}$ ascertained from the physically motivated sensor model 21 is applied in a correction block 23 in order to obtain a corrected concentration variable $C_{korr}$. In particular, the correction variable K may be a correction factor to be multiplied with the raw concentration variable $C_{phys}$ or a correction offset to be added to the raw concentration variable $C_{phys}$.

The correction variable K may be ascertained by a data-based sensor model in sensor model block 22. The data-based sensor model may comprise a regression model, such as a Lasso model, a random forest model, a Gaussian process model or a neural network, for example.

Selected ones of the measurement variables M1, M2, M3 . . . and measurement features F1, F2, F3 . . . derived therefrom may be used as input variables for the sensor model.

The data-based sensor model ascertains the correction variable K from one or more of the above measurement variables M1, M2, M3 . . . .

The measurement features F1, F2, F3 . . . may be derived in measurement feature block 24 from the measurement variables M1, M2, M3 and serve to compress the information contained in the measurement variables. For example, measurement features F1, F2, F3 . . . may comprise one or more of the following measurement features:

a signal response triggered by application of a test voltage pulse, a proportionality factor between the temperature and the sensor signal and/or a time constant of the signal response;

signal responses triggered by sudden changes in the composition (particularly humidity) and/or pressure of the sample gas meeting sensor surface 31. These changes occur especially at the start or end of the measurement process when the gas composition is changed;

a baseline value corresponding to a raw gas sensor signal at a defined point in time (e.g., at the time of the start of the measurement process);

one or more parameters of physical models that are fitted to the measurement data. For example, a model of the adsorption and desorption kinetics may be fitted to the sensor signal during the exposure phase and a possible subsequent holding phase, and the fitted physical parameters (e.g., adsorption enthalpy, rate constant) used as a measurement feature for the sensor model.

a parameter of empirical relationships that are fitted to the measurement data, such as a parameter of an exponential function that is fitted to the sensor signal during the heating-up or cooling-down phase, for example.

modified measurement variables, in particular by compensation of the influence of temperature on the raw gas sensor signal using a corresponding proportionality factor;

one or more discrete values of the sensor signals in time periods before or after the measurement process as a function of the temperature sensor values converted from relative to absolute gas humidity using the Antoine equation a difference or quotient between successively detected values of at least one of the measurement variables of at least one of the measurement variables, in particular a difference or quotient between successively detected values of at least one of the measurement variables between a current value of the at least one measurement variable and a reference value of the at least one measurement variable.

The data-based sensor model is trained with training data which assign measurement features to an associated concentration variable (ground truth). The measurement features are obtained from measurement variables of gas sensor 3, exposed in each case to a calibration sample gas. The concentration variable corresponds in each case to the gas concentration in the calibration sample gas, the gas sensors 3 having been stored under different storage conditions. By calculating back from the concentration variable obtained from the physically motivated model, the data-based sensor model may be correlated accordingly.

To train the data-based sensor model, experimentally labeled pairs of measurement variables and measurement features and gas concentration may be generated by varying storage histories, i.e., temporal sequences of environmental conditions, for example by varying the storage period, temperature and atmospheric humidity in a controlled manner, and by using calibration sample gases with a known concentration of the gas component to be detected.

Figure 3:
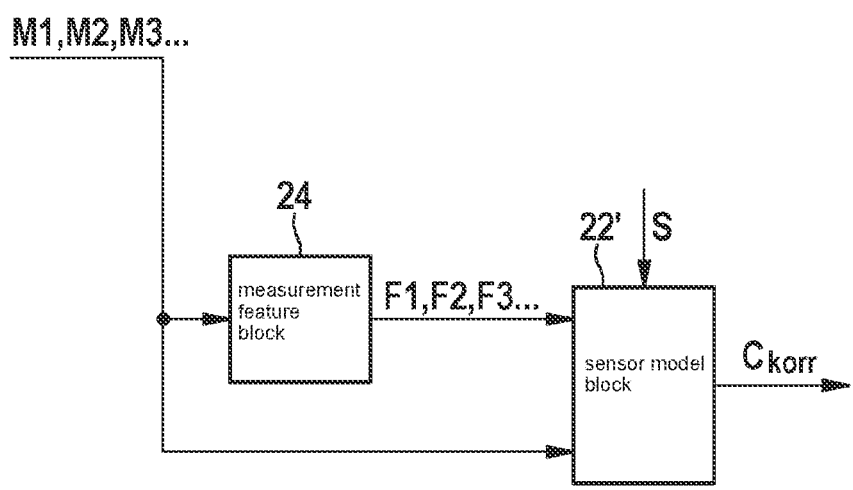
FIG. 3 shows a functional block diagram for determining a gas concentration using a gas sensor according to a further specific embodiment of the present invention.

According to an alternative specific embodiment, as shown in the functional diagram of FIG. 3, the data-based sensor model may directly ascertain the corrected concentration variable $C_{korr}$ in a sensor model block 22'. In this case, the physical sensor model is implemented in the data-based sensor model together with the correction, depending on the respective sensor state, in order to ascertain the corrected concentration variable $C_{korr}$ as a model output.

In a hybrid model approach, the physical sensor model and the data-based sensor model may determine corrected concentration variables in parallel. With the aid of a subsequent weighting function, the two corrected concentration variables may be weighted in respect of each other, it being possible to choose the weighting depending on the corrected concentration variables in each case, in particular in accordance with a predefined weighting function.

What is claimed is:

1. A method for operating a gas sensor system including a gas sensor, to provide a concentration variable of a gas concentration of a gas component in a sample gas, the method comprising the following steps:
   measuring the gas concentration during a measurement process to obtain a temporal evolution of a sensor signal as a function of the gas concentration; and
   determining the concentration variable using a data-based sensor model as a function of the temporal evolution of the sensor signal, the data-based sensor model being trained to take into account a behavior of the sensor outside the measurement process, to ascertain the concentration variable;
   wherein the concentration variable is determined using one or more variables as input to the data-based sensor model, the one or more variables including:
   values of the sensor signal generated by the gas sensor during a heating-up phase;
   values of the sensor signal generated by the gas sensor during a cooling-down phase;
   an absolute signal change in the sensor signal between a start and an end of the measurement process;
   a maximum increase of the sensor signal during the measurement process;
   an average increase of the sensor signal during the measurement process;
   an absolute change in the sensor signal between a start and an end of a predefined period outside of the measurement process;
   a maximum increase of the sensor signal over the predefined period outside of the measurement process;
   an average increase of the sensor signal over the predefined period outside of the measurement process;
   an absolute change in the sensor signal between a start and an end of the measurement process;
   a maximum increase of a signal of one more other sensors integrated in the system over the predefined period outside of the measurement process;
   a maximum increase of a signal of one more other sensors integrated in the system over a course of the measurement process;
   an average increase of the signal of the one more other sensors integrated in the system over the course of the measurement process;
   a maximum increase of the signal of one more other sensors integrated in the system over the predefined period outside of the measurement process;
   an average increase of the signal of the one more other sensors integrated in the system over the predefined period outside of the measurement process;
   an indication of a signal response triggered by application of a test voltage pulse;
   a proportionality of a change in a temperature to a change in the sensor signal;
   a measure of a response time of the sensor signal to a change in the gas concentration;
   a response of the sensor signal to a change in pressure of a sample gas meeting a surface of the gas sensor;
   one or more modified measurement variables obtained by applying to the sensor signal a proportionality factor that corresponds to an influence of temperature on the sensor signal; and/or
   one or more discrete values of the sensor signal in the predefined period outside of the measurement process as a function of the temperature.

2. The method as recited in claim 1, wherein the data-based sensor model includes a Gaussian process model, or a LASSO algorithm, or a random forest algorithm, or a neural network, and the data-based sensor model is trained to take into account a sensor behavior influenced by an aging or degradation of the gas sensor to ascertain the concentration variable.

3. The method as recited in claim 1, wherein the data-based sensor model is used to ascertain a correction variable to be applied to a physically modeled concentration variable by multiplication or addition, the physically modeled concentration variable being determined on based on measurement variables associated with the measurement process.

4. The method as recited in claim 1, wherein the concentration variable is ascertained as a function of a physically modeled concentration variable and as a function of a concentration variable ascertained using the data-based sensor model, in accordance with a predefined weighting function.

5. The method as recited in claim 1, wherein the concentration variable is determined using as at least part of the input to the data-based sensor model the values of the sensor signal generated by the gas sensor during the heating-up phase.

6. The method as recited in claim 5, wherein the concentration variable is determined using as at least part of the input to the data-based sensor model a parameter of an exponential function that is fitted to the sensor signal during the heating-up phase.

7. The method as recited in claim 1, wherein the concentration variable is determined using as at least part of the input to the data-based sensor model the values of the sensor signal generated by the gas sensor during the cooling-down phase.

8. The method as recited in claim 7, wherein the concentration variable is determined using as at least part of the input to the data-based sensor model a parameter of an exponential function that is fitted to the sensor signal during the cooling-down phase.

9. The method as recited in claim 1, wherein the concentration variable is determined using as at least part of the input to the data-based sensor model the absolute signal change in the sensor signal between the start and the end of the measurement process.

10. The method as recited in claim 1, wherein the concentration variable is determined using as at least part of the input to the data-based sensor model the maximum increase of the sensor signal during the measurement process.

11. The method as recited in claim 1, wherein the concentration variable is determined using as at least part of the input to the data-based sensor model the average increase of the sensor signal during the measurement process.

12. The method as recited in claim 1, wherein the concentration variable is determined using as at least part of the input to the data-based sensor model the absolute change in the sensor signal between the start and the end of the predefined period outside of the measurement process.

13. The method as recited in claim 1, wherein the concentration variable is determined using as at least part of the input to the data-based sensor model the maximum increase of the sensor signal over the predefined period outside of the measurement process.

14. The method as recited in claim 1, wherein the concentration variable is determined using as at least part of the input to the data-based sensor model the average increase of the sensor signal over the predefined period outside of the measurement process.

15. The method as recited in claim 1, wherein the concentration variable is determined using as at least part of the input to the data-based sensor model the absolute change in the sensor signal between the start and the end of the measurement process.

16. The method as recited in claim 1, wherein the concentration variable is determined using as at least part of the input to the data-based sensor model the maximum increase of the signal of one more other sensors integrated in the system over the predefined period outside of the measurement process.

17. The method as recited in claim 1, wherein the concentration variable is determined using as at least part of the input to the data-based sensor model the maximum increase of the signal of one more other sensors integrated in the system over the course of the measurement process.

18. The method as recited in claim 1, wherein the concentration variable is determined using as at least part of the input to the data-based sensor model the average increase of the signal of the one more other sensors integrated in the system over the course of the measurement process.

19. The method as recited in claim 1, wherein the concentration variable is determined using as at least part of the input to the data-based sensor model the maximum increase of the signal of the one more other sensors integrated in the system over the predefined period outside of the measurement process.

20. The method as recited in claim 1, wherein the concentration variable is determined using as at least part of the input to the data-based sensor model the average increase of the signal of the one more other sensors integrated in the system over the predefined period outside of the measurement process.

21. The method as recited in claim 1, wherein the concentration variable is determined using as at least part of the input to the data-based sensor model the indication of the signal response triggered by application of the test voltage pulse.

22. The method as recited in claim 1, wherein the concentration variable is determined using as at least part of the input to the data-based sensor model the proportionality of the change in the temperature to the change in the sensor signal.

23. The method as recited in claim 1, wherein the concentration variable is determined using as at least part of the input to the data-based sensor model the measure of the response time of the sensor signal to the change in the gas concentration.

24. The method as recited in claim 1, wherein the concentration variable is determined using as at least part of the input to the data-based sensor model the response of the sensor signal to the change in pressure of the sample gas meeting the surface of the gas sensor.

25. The method as recited in claim 1, wherein the concentration variable is determined using as at least part of the input to the data-based sensor model the one or more modified measurement variables obtained by applying to the sensor signal the proportionality factor that corresponds to the influence of temperature on the sensor signal.

26. The method as recited in claim 1, wherein the concentration variable is determined using as at least part of the input to the data-based sensor model the one or more discrete values of the sensor signal in the predefined period outside of the measurement process as the function of the temperature.

27. The method as recited in claim 1, wherein the concentration variable is determined using as at least part of the input to the data-based sensor model for each of one or more of the variables, a difference or quotient between successively detected values of the respective variable.

28. The method as recited in claim 1, wherein the concentration variable is determined using as at least part of the input to the data-based sensor model for each of one or more of the variables, a difference or quotient between a detected value of the respective variable and a respective reference value.

29. A device configured to operate a gas sensor system including a gas sensor, to provide a concentration variable of a gas concentration of a gas component in a sample gas, the device being configured to:
measure the gas concentration during a measurement process to obtain a temporal evolution of a sensor signal as a function of the gas concentration; and
determine the concentration variable using a data-based sensor model as a function of the temporal evolution of the sensor signal, the data-based sensor model being trained to take into account a behavior of the sensor outside the measurement process to ascertain the concentration variable;
wherein the concentration variable is determined using one or more variables as input to the data-based sensor model, the one or more variables including:
values of the sensor signal generated by the gas sensor during a heating-up phase;
values of the sensor signal generated by the gas sensor during a cooling-down phase;
an absolute signal change in the sensor signal between a start and an end of the measurement process;
a maximum increase of the sensor signal during the measurement process;
an average increase of the sensor signal during the measurement process;
an absolute change in the sensor signal between a start and an end of a predefined period outside of the measurement process;
a maximum increase of the sensor signal over the predefined period outside of the measurement process;
an average increase of the sensor signal over the predefined period outside of the measurement process;
an absolute change in the sensor signal between a start and an end of the measurement process;

a maximum increase of a signal of one more other sensors integrated in the system over the predefined period outside of the measurement process;
a maximum increase of a signal of one more other sensors integrated in the system over a course of the measurement process;
an average increase of the signal of the one more other sensors integrated in the system over the course of the measurement process;
a maximum increase of the signal of one more other sensors integrated in the system over the predefined period outside of the measurement process;
an average increase of the signal of the one more other sensors integrated in the system over the predefined period outside of the measurement process;
an indication of a signal response triggered by application of a test voltage pulse;
a proportionality of a change in a temperature to a change in the sensor signal;
a measure of a response time of the sensor signal to a change in the gas concentration;
a response of the sensor signal to a change in pressure of a sample gas meeting a surface of the gas sensor;
one or more modified measurement variables obtained by applying to the sensor signal a proportionality factor that corresponds to an influence of temperature on the sensor signal; and/or
one or more discrete values of the sensor signal in the predefined period outside of the measurement process as a function of the temperature.

30. A gas sensor system, comprising:
a gas sensor; and
a device configured to provide a concentration variable of a gas concentration of a gas component in a sample gas, the device being configured to:
  measure the gas concentration during a measurement process to obtain a temporal evolution of a sensor signal as a function of the gas concentration; and
  determine the concentration variable using a data-based sensor model as a function of the temporal evolution of the sensor signal, the data-based sensor model being trained to take into account a behavior of the sensor outside the measurement process to ascertain the concentration variable;
wherein the concentration variable is determined using one or more variables as input to the data-based sensor model, the one or more variables including:
  values of the sensor signal generated by the gas sensor during a heating-up phase;
  values of the sensor signal generated by the gas sensor during a cooling-down phase;
  an absolute signal change in the sensor signal between a start and an end of the measurement process;
  a maximum increase of the sensor signal during the measurement process;
  an average increase of the sensor signal during the measurement process;
  an absolute change in the sensor signal between a start and an end of a predefined period outside of the measurement process;
  a maximum increase of the sensor signal over the predefined period outside of the measurement process;
  an average increase of the sensor signal over the predefined period outside of the measurement process;
  an absolute change in the sensor signal between a start and an end of the measurement process;
  a maximum increase of a signal of one more other sensors integrated in the system over the predefined period outside of the measurement process;
  a maximum increase of a signal of one more other sensors integrated in the system over a course of the measurement process;
  an average increase of the signal of the one more other sensors integrated in the system over the course of the measurement process;
  a maximum increase of the signal of one more other sensors integrated in the system over the predefined period outside of the measurement process;
  an average increase of the signal of the one more other sensors integrated in the system over the predefined period outside of the measurement process;
  an indication of a signal response triggered by application of a test voltage pulse;
  a proportionality of a change in a temperature to a change in the sensor signal;
  a measure of a response time of the sensor signal to a change in the gas concentration;
  a response of the sensor signal to a change in pressure of a sample gas meeting a surface of the gas sensor;
  one or more modified measurement variables obtained by applying to the sensor signal a proportionality factor that corresponds to an influence of temperature on the sensor signal; and/or
  one or more discrete values of the sensor signal in the predefined period outside of the measurement process as a function of the temperature.

31. An non-transitory electronic storage medium on which is stored a computer program for operating a gas sensor system including a gas sensor, to provide a concentration variable of a gas concentration of a gas component in a sample gas, the computer program, when executed by a computer, causing the computer to perform the following steps:
  measuring the gas concentration during a measurement process to obtain a temporal evolution of a sensor signal as a function of the gas concentration; and
  determining the concentration variable using a data-based sensor model as a function of the temporal evolution of the sensor signal, the data-based sensor model being trained to take into account a behavior of the sensor outside the measurement process, to ascertain the concentration variable;
wherein the concentration variable is determined using one or more variables as input to the data-based sensor model, the one or more variables including:
  values of the sensor signal generated by the gas sensor during a heating-up phase;
  values of the sensor signal generated by the gas sensor during a cooling-down phase;
  an absolute signal change in the sensor signal between a start and an end of the measurement process;
  a maximum increase of the sensor signal during the measurement process;
  an average increase of the sensor signal during the measurement process;
  an absolute change in the sensor signal between a start and an end of a predefined period outside of the measurement process;
  a maximum increase of the sensor signal over the predefined period outside of the measurement process;

an average increase of the sensor signal over the predefined period outside of the measurement process;

an absolute change in the sensor signal between a start and an end of the measurement process;

a maximum increase of a signal of one more other sensors integrated in the system over the predefined period outside of the measurement process;

a maximum increase of a signal of one more other sensors integrated in the system over a course of the measurement process;

an average increase of the signal of the one more other sensors integrated in the system over the course of the measurement process;

a maximum increase of the signal of one more other sensors integrated in the system over the predefined period outside of the measurement process;

an average increase of the signal of the one more other sensors integrated in the system over the predefined period outside of the measurement process;

an indication of a signal response triggered by application of a test voltage pulse;

a proportionality of a change in a temperature to a change in the sensor signal;

a measure of a response time of the sensor signal to a change in the gas concentration;

a response of the sensor signal to a change in pressure of a sample gas meeting a surface of the gas sensor;

one or more modified measurement variables obtained by applying to the sensor signal a proportionality factor that corresponds to an influence of temperature on the sensor signal; and/or one or more discrete values of the sensor signal in the predefined period outside of the measurement process as a function of the temperature.

\* \* \* \* \*